(12) United States Patent
Meiser et al.

(10) Patent No.: US 8,940,518 B2
(45) Date of Patent: Jan. 27, 2015

(54) PHOTOBIOREACTOR

(71) Applicant: Aveston Grifford Ltd., Vg-Tortola (VG)

(72) Inventors: Andreas Meiser, Stuttgart (DE); Miguel Verhein, London (GB)

(73) Assignee: Aveston Grifford Ltd., Vg-Tortola (VG)

( * ) Notice: Subject to any disclaimer, the term of this patent is extended or adjusted under 35 U.S.C. 154(b) by 0 days.

(21) Appl. No.: 14/270,694

(22) Filed: May 6, 2014

(65) Prior Publication Data

US 2014/0242677 A1   Aug. 28, 2014

Related U.S. Application Data

(62) Division of application No. 12/812,569, filed as application No. PCT/IB2009/000076 on Jan. 19, 2009.

(30) Foreign Application Priority Data

| Jan. 18, 2008 | (DE) | 10 2008 004 932 |
| Jan. 18, 2008 | (DE) | 10 2008 004 933 |
| Jul. 4, 2008 | (WO) | PCT/IB2008/001770 |

(51) Int. Cl.
  C12M 1/09 (2006.01)
  C12M 1/00 (2006.01)
  C12N 1/12 (2006.01)
  C12M 1/34 (2006.01)

(52) U.S. Cl.
  CPC .................. C12N 1/12 (2013.01); C12M 21/02 (2013.01); C12M 23/26 (2013.01); C12M 23/34 (2013.01); C12M 23/56 (2013.01); C12M 41/12 (2013.01); C12M 41/32 (2013.01)
  USPC ...................... 435/243; 435/289.1; 435/292.1

(58) Field of Classification Search
  None
  See application file for complete search history.

(56) References Cited

U.S. PATENT DOCUMENTS

| 3,955,317 A | 5/1976 | Gudin |
| 4,868,123 A | 9/1989 | Berson et al. |
| 4,924,698 A | 5/1990 | Echert et al. |
| 4,958,460 A | 9/1990 | Nielson et al. |
| 6,171,480 B1 | 1/2001 | Lee et al. |
| 7,980,024 B2 | 7/2011 | Berzin et al. |

FOREIGN PATENT DOCUMENTS

| WO | WO-2005121309 | 6/2005 |
| WO | WO-2008134010 | 11/2008 |
| WO | WO-2008153202 | 12/2008 |

*Primary Examiner* — John S Brusca
*Assistant Examiner* — Sharon M Papciak
(74) *Attorney, Agent, or Firm* — Gifford, Krass, Sprinkle, Anderson & Citkowski, P.C.

(57) ABSTRACT

A method of operating a closed photobioreactor for cultivation of phototrophic microorganisms. The photobioreactor comprises a culture liquid and is partially or completely surrounded by water of a water body. A density difference between the culture liquid and the surrounding water is provided so that the position of the photobioreactor in the water body is controlled. A closed photobioreactor for cultivation of phototrophic microorganisms. The photobioreactor is adapted to comprise a culture liquid and to be partially or completely surrounded by water of a water body. The photobioreactor comprises means for determining the density difference between the culture liquid and the surrounding water.

20 Claims, 7 Drawing Sheets

PHOTOBIOREACTOR

REFERENCE TO RELATED APPLICATIONS

This application is a continuation of U.S. patent application Ser. No. 12/812,569, filed Nov. 8, 2010, which is a U.S. national stage of PCT/IB2009/000076, filed Jan. 19, 2009, the entire content of both of which is incorporated herein by reference.

TECHNICAL FIELD

The present invention relates to a method of operating a closed photobioreactor for cultivation of phototrophic microorganisms and to a closed photobioreactor for cultivation of phototrophic microorganisms.

BACKGROUND ART

It is known that phototrophic microorganisms are already today found in many commercial applications. Thus, algae are produced to manufacture β-carotene, astaxanthin, etc., or the complete algae biomass is sold as nutritional supplement. Today, the production of algae biomass faces two main difficulties. First, a large part of the current production results from open systems (e.g., so-called open ponds). These open systems are sensitive for contaminations by other algae strains or by pest, therefore only algae with very specific growth requirements can be grown in these systems. Thus, for instance the algae *Dunaliella* is cultured for the production of β-carotene under very saline conditions, which are not suited for most other organisms. Second, the production costs of algae biomass is rather high (>USD 2,000 per metric ton), so that a commercial production for many applications, especially in the energy sector or the transportation sector, is not profitable. In particular, production costs are often increasing even more if closed systems are used instead of open systems to avoid contaminations. Besides the open ponds, a large number of various photobioreactor types are presently in use. Tube reactors, which can consist of one or more horizontal tubes, or wherein a tube is helically wound around a cylinder or cone (biocoil), are among the best known. Furthermore, flat panel reactors are often used, such reactors providing a vertical liquid layer for cultivation of algae.

The main challenges in the production of chemicals and energy from algae are the risk of contamination and the high cost for the manufacturing of the algae biomass. Likewise, the main challenges in the production of fine chemicals, nutritional supplements, vitamins, omega-3-fatty acids, antioxidants (e.g. carotenoids), pharmaceutically active substances or dried biomass for nutritional supplementation from algae are thus the risk of contamination and the high cost for the manufacturing of the biomass. The same challenges apply when culturing algae for biofuels, animal feed, amino acids, methane production, etc.

WO 2005/121309 discloses a device for algae production, in which a fluid comprising algae is located in growth containers, to which a gas containing $CO_2$ is supplied, the gas being circulated through the containers via a gas-conditioning apparatus. In an embodiment the containers are made of a double plastic sheet forming a sheet bag. In an embodiment said to be suitable for the production of micro-algae in the sea, a welded-together sheet bag is placed to float horizontally in the water surface.

U.S. Pat. No. 4,868,123 discloses an apparatus for production of microorganisms by photosynthesis. The apparatus comprises a bioreactor to be placed on an expanse of water, which has a first group of flexible tubes, which are transparent to light and in which the culture medium circulated and a second group of inflatable tubes, disposed and maintained beneath the first group by means of detachable Y-shaped interpolated members, which are regularly spaced. According to this document, when the temperature of the culture medium exceeds an upper reference temperature the photobioreactor is immersed through deflation of the tubes of the second group. Conversely, when the temperature of the medium is below a minimum reference temperature, the tubes of the second group are inflated with compressed air. The immersion of the photobioreactor can also be ensured by introducing a relatively heavy liquid into the tubes of the second group, whilst floating can be ensured by injecting a light fluid other than air.

Since large-scale cultivation of microorganisms is very cost sensitive, there is a demand for simpler and cheaper bioreactor arrangements.

SUMMARY OF THE INVENTION

Today, the cultivation of phototrophic microorganisms is characterized by high cost for the production of biomass. The new photobioreactor will be able to significantly reduce production costs for biomass. Additionally, by a closed process design the risk of contamination as compared to open systems can be strongly reduced.

In order to avoid contamination, a closed photobioreactor will be used, which may, e.g. be produced from a plastic such as polyethylene. A strong reduction of costs is achieved as the photobioreactor swims in or upon a water body, e.g. an artificial pond. By this construction principle, costs are avoided for levelling out the photobioreactor exactly horizontally. As the hydrostatic inner pressure of the photobioreactor is partly compensated by the surrounding water, the strength of the walls of the photobioreactor can be reduced or a less stable material can be used. The water surrounding the photobioreactor is able to supply or remove heat, making an additional thermoregulation redundant. By using a flexible material for the photobioreactor, as well as the possibility of changing the position of the photobioreactor in the surrounding water body and the possibility of changing the layer thickness of culture liquid, the operational conditions of the photobioreactor can be adapted according to environmental factors such as solar radiation or temperature, what should increase the productivity leading to a further reduction of costs. By the possibility of operating the photobioreactor on water surfaces, a very large area is available to realize such a photobioreactor system, considering that our planet is by more than 70% covered by water.

The described photobioreactor may serve for production of biomass from phototrophic organisms, which can be used for manufacture of any type of biofuels, animal feed, proteins, amino acids, for basic human nutrition as well as for production of biomass from phototrophic organisms, which is used for manufacture of fine chemicals, nutritional supplements, vitamins, omega-3-fatty acids, antioxidants (e.g., carotenoids), pharmaceutically active substances ingredients, or dried biomass for use as nutritional supplement.

Thus, an object of the present invention is to facilitate temperature regulation of the contents, such as culture medium and microorganisms cultured therein, of a closed photobioreactor. A related object of the invention is to utilise the cooling capacity of water surrounding, partially or fully, a closed photobioreactor in order to regulate the temperature of its contents.

Another object of the present invention is to allow for control of the vertical position of a closed photobioreactor surrounded, partially or fully, by water. In particular, it is an object of the invention to allow for such position control without a need for other buoyancy regulating means than the contents, e.g. the culture medium, of the photobioreactor itself and the surrounding water.

Yet another object of the present invention is to provide a photobioreactor which automatically gives a homogenous distribution of the thickness of the culture liquid when the photobioreactor is floating on a water body.

Since the photobioreactor of the present invention, or parts thereof, may preferably be made of a flexible material, the shape of the reactor may be influenced by internal and external impacts and inhomogenities. Hence, in order to retain the shape and optimal function of the photobioreactor, the control of such impacts and inhomogenities may be important. Therefore it is an object of the present disclosure to provide means for additional control of the position and/or shape of the flexible photobioreactor.

A further object of the present invention is to simplify the construction, and lower the cost, of a closed photobioreactor and its peripheral equipment.

Other objects or advantages of the invention should be apparent to a person skilled in the art after having read the description below.

The term photobioreactor, as used herein, generally refers to the compartment of the photobioreactor which is adapted to comprise the algae culture liquid, and in which photosynthesis occurs, including any additional compartments or tubes, sub-compartments or mechanical means for controlling the position and/or shape of the photobioreactor, but the term may also refer to a photobioreactor system in a wider sense, comprising said algae compartment including any additional compartments or tubes, sub-compartments or mechanical means for controlling the position and/or shape of the photobioreactor, as well as periferal equipment such as e.g. pumps, hoses, tanks and other equipment required for operating the reactor.

In a first aspect of the invention, there is provided a method of operating a closed photobioreactor for cultivation of phototrophic microorganisms, the photobioreactor comprising a culture liquid and the photobioreactor being partially or completely surrounded by water of a water body, wherein a density difference between the culture liquid and the surrounding water is provided so that the position of the photobioreactor in the water body is controlled.

The main principle on which the present invention is based is the ability to control the vertical position of a flexible and light weight photobioreactor in a surrounding water body by controlling the density of the photobioreactor versus the density of the surrounding water, e.g. by providing different salinity concentrations inside and outside of the reactor. It has been shown that a reactor containing fresh or brackish water (low density) floats easily on a water body consisting of salt water (high density). Furthermore it has been found that a photobioreactor according to the present invention stabilizes itself, meaning that it assumes a perfect horizontal position regardless of the position it was placed in at the beginning of the experiment, and that the thickness of the layer of culture liquid inside the reactor becomes very homogenous, again independent of the starting point. Thus, in a case where the photobioreactor contains fresh water and the surrounding water body comprises salt water, by using different salinities in the reactor itself and in the surrounding water body and thereby different densities in the two water bodies, a stable fresh water lens confined by the flexible transparent walls of the photobioreactor will form on the surrounding salt-water body.

The inventive concept of using the density difference to stabilize the reactor and to obtain a homogenous thickness of the culture liquid layer allows for the provision of a very simple and extremely cost efficient photobioreactor system. Firstly, the fresh water in the system will form the optimal (horizontal) structure itself, meaning that a thin and low cost material can be used for the reactor. Secondly, the reactor will automatically move into a position, which is optimal for growing algae, thereby minimizing the need for mechanical equipment or process control devices to arrange the reactor in the preferred position. Thirdly, the homogenous thickness of the culture liquid layer, as well as the possibility of optimizing the thickness of the culture liquid layer by varying the amount of culture liquid in the photobioreactor, allows for high biomass density in the culture liquid, meaning that the photobioreactor according to the present invention may contain more biomass and therefore have a higher energy efficiency.

Since small density differences in the water inside and outside of the photobioreactor caused by a difference in salinity and/or temperature are the only driving forces for moving the reactor, it is preferable to have a thin and flexible material in the walls of the photobioreactor. Having thin and flexible walls will optimize the capability of the photobioreactor to self stabilize. An example of a material which is suitable for use in the photobioreactor walls is polyethylene or equivalent material with a thickness of about 0.1 mm.

By provision of said density difference between the culture liquid and the surrounding water so that the position of the photobioreactor in the water body is controlled is thus created a change in buoyancy of the photobioreactor in relation to the surrounding water, this change in buoyancy being the driving force of a vertical position change of the reactor. Thus, the density difference provided takes into account the weight and buoyancy of the photobioreactor itself. Accordingly, the present invention represents a simple and cheap solution in order to control the position of the photobioreactor in surrounding water. Likewise, cooling of the contents of the photobioreactor may be achieved efficiently and at low cost by lowering the photobioreactor in the surrounding water.

Furthermore, the closed process design of the system reduces significantly the risk of contaminations. The fact that the photobioreactor is (partially) surrounded by water reduces production costs by various effects: By having the photobioreactor floating or hovering in water, no costly construction works are required to level out the terrain. The photobioreactor floats or hovers as a closed system in the surrounding water body, therefore a pool representing the surrounding water body may be prepared in very simple and cost efficient manner. In the extreme, even rivers, lakes, the sea, or water-filled natural clay pits can be used as external water body. The surrounding water body can optimally provide and remove heat, therefore no costs for further thermoregulation need to be met. As the hydrostatic inner pressure of the photobioreactor is partially compensated by the surrounding water, the thickness of the photobioreactor walls can be reduced or a less stable material could be used, what contributes to a further cost reduction.

By the flexible construction of the photobioreactor, i.e. the possibility to change the position of the reactor in the surrounding water body and the possibility to change the thickness of the culture liquid in the photobioreactor, the process parameters of the photobioreactor can be adapted according to environmental conditions such as intensity of solar radiation and temperature, which will lead to an increase of productivity and will reduce the costs further. The thickness of the culture liquid influences the light path for the sun light necessary for growth of the phototrophic organisms.

As the photobioreactor can be operated on water surfaces, a very large area is available for realization of such a photobioreactor system, since our planet is covered to more than 70% by water.

The density difference may be provided by provision of a salinity difference between the culture liquid and the surrounding water. Said salinity difference may be provided by increasing or decreasing the salinity of the culture liquid. Said salinity difference may also, or alternatively, be provided by increasing or decreasing the salinity of the surrounding water, in particular the surrounding water of a closed water body. In this context, as the skilled man understands, the term "closed water body" refers to well-defined systems of water allowing control of, e.g. the amount or type, such as fresh, brackish or salt, of water therein. Examples of closed bodies of water are natural or artificial ponds or pools. A salinity increase of the culture liquid may be provided simultaneously as a salinity decrease of the surrounding water is provided. A salinity decrease of the culture liquid may be provided simultaneously as a salinity increase of the surrounding water is provided.

The density difference may be provided by provision of a temperature difference between the culture liquid and the surrounding water. Said temperature difference may be provided by changing the temperature of the surrounding water, in particular the surrounding water of a closed water body. The meaning of "closed water body" is as above.

The density difference may be provided by an increase or decrease of a gas pressure of the culture liquid. Thus, the density of the culture liquid may be influenced by the pressure of gas supplied to the photobioreactor in order to be consumed (e.g. carbon dioxide) by the algae or by the pressure of a gas produced (e.g. oxygen) by the algae.

Salinity, temperature, gas pressure and/or other parameters influencing the density of the culture liquid and/or the surrounding water may be modified separately or simultaneously in order to provide a desirable density difference. The density of the culture liquid and the density of the surrounding water may be modified separately or simultaneously in order to provide a desirable density difference.

The density difference may be provided so that the density of the culture liquid is increased or so that the density of the surrounding water is decreased, whereby the position of the photobioreactor in the water body is lowered. The density difference may be provided so that the density of the culture liquid is decreased or so that the density of the surrounding water is increased, whereby the position of the photobioreactor in the water body is raised. The density difference may be provided so that the position of the photobioreactor in the water body is maintained. Again, the density of the culture liquid and the density of the surrounding water may be modified simultaneously in order to provide a desirable density difference, either for lowering, raising or maintaining the position of the photobioreactor.

The above-described method of operating a photobioreactor, i.e. a method wherein a density difference between the culture liquid and the surrounding water is provided so that the position of the photobioreactor in the water body is controlled, is particularly suitable for long-term control of the position. In this context, "long-term control of the position" refers to position changes (raising or lowering of the photobioreactor) that need not be reversed within several hours or days from initiation of the change. However, in the inventive method, the photobioreactor may be equipped with one or more compartments or tubes adapted to further control the buoyancy of the photobioreactor. Advantages of such compartments or tubes are stated below.

In the inventive method, the photobioreactor may also be equipped with mechanical means adapted to further control the vertical position and/or shape of the photobioreactor. Such mechanical means and the advantages thereof are discussed below.

In the inventive method, the photobioreactor may have a flat panel shape. In comparison to, e.g., tube-shaped photobioreactors, a flat panel reactor requires less construction material, requires less energy input due to lower flow resistance, and has less restrictions on scalability.

In the inventive method, the photobioreactor may further comprise additional features as described below in respect of the second aspect of the invention.

In a second aspect of the invention, there is provided a closed photobioreactor for cultivation of phototrophic microorganisms, the photobioreactor being adapted to comprise a culture liquid and the photobioreactor being adapted to be partially or completely surrounded by water of a water body, wherein the photobioreactor comprises means for determining the density difference between the culture liquid and the surrounding water.

Since small density differences in the water inside and outside of the photobioreactor caused by a difference in salinity and/or temperature are the only driving forces for moving the reactor, it is preferable to have a thin and flexible material in the walls of the photobioreactor. Having thin and flexible walls will optimize the capability of the photobioreactor to self stabilize.

The closed photobioreactor may preferably comprise a compartment, referred to herein as the algae compartment, confined by walls of a water tight, transparent and flexible material.

The water tight, transparent and flexible material may preferably further be a light weight, or low density, material. The material may preferably be a polymer based material, such as a thin film of a polyolefin based polymer, e.g. polyethylene or polypropylene. Other polymers suitable for use with the present invention will be readily recognized by a person skilled in the art of polymeric materials. The thickness of the walls should be selected depending on the properties, such as flexibility, transparency and durability, of the specific material used and may for example be in the range of 10-1000 μm or in the range of 25-500 μm or in the range of 50-150 μm. It is preferred, with regard taken to the durability of the material, to make the walls of the photobioreactor as thin as possible in order to maximize the flexibility and transparency. As a non-limiting example, a polyethylene film having a thickness of about 100 μm has been found to be suitable for use in the walls of the photobioreactor.

The algae compartment of the photobioreactor may as an example comprise a top sheet and a bottom sheet of the water tight transparent and flexible material attached to each other such that a closed compartment is formed between the two sheets, but other arrangements resulting in a sealed compartment confined by walls of a water tight transparent, flexible and light weight material are also considered.

The algae compartment of the photobioreactor may further comprise various inlet and outlet ports, to which may be connected hoses, pumps, liquid or gas sources and other additional equipment required or useful to the operation of the photobioreactor.

The means for determining the density difference may comprise means for determining the salinity and/or the temperature of the culture liquid. The means for determining the density difference may comprise means for determining the salinity and/or the temperature of the surrounding water. Suitable means for determining the salinity of the culture liquid or the surrounding water may be identified by a skilled man and their function may, e.g., be based on measurement of conductivity of the medium in which the salinity is to be determined. Suitable means for determining the temperature of the culture liquid or the surrounding water may be identified by a skilled man and may for example be a thermocouple or another device for temperature measurement providing an electrical signal representing the temperature.

The photobioreactor may be equipped with one or more additional compartments or tubes adapted to further control the buoyancy of the photobioreactor. The compartments or tubes may contain gas, water or any other liquid. Thus, the additional compartments or tubes increase the speed at which the position of the photobioreactor in the water body is controlled. The additional compartment(s) or tube(s) may therefore be used when the position of the photobioreactor needs to be adapted quickly, such as in response to short-term changes of the temperature of the culture liquid. By "short-term changes" is referred to changes on the minute or hour scale.

The photobioreactor may be equipped with mechanical means for accelerating submersion or floatation when the position of the photobioreactor needs to be adapted quickly, e.g. for optimizing the growth conditions of the algae, e.g. the temperature, or due to weather related conditions such as strong winds. Such mechanical means may e.g. comprise a net or at least one elongated member, such as a rope, cable or rod, stretched above the photobioreactor and arranged to be brought down or up to assist the submersion or floatation of the photobioreactor. Such a net or at least one elongated member may or may not be fixed to the surface of the photobioreactor. Generally it will be useful to have two or more elongated members arranged in parallel and distributed at suitable distances across the length of the photobioreactor. The elongated members may be brought down or up simultaneously or in sequence, e.g. such that the entire photobioreactor is submerged simultaneously, or such that one side of the reactor is submerged first and the other side of the reactor is submerged subsequently.

The photobioreactor may have a flat panel shape. In comparison to, e.g., tube-shaped photobioreactors, a flat panel reactor requires less construction material, requires less energy input due to lower flow resistance, and has less restrictions on scalability.

The algae compartment of the photobioreactor may also comprise two or more sub-compartments adapted to comprise the culture liquid. Said sub-compartments may be adapted to comprise a portion of the culture liquid present in the photobioreactor. Preferably, when the photobioreactor comprises two or more such sub-compartments, the culture liquid may be distributed evenly between sub-compartments. The use of sub-compartments in the photobioreactor may help stabilize the reactor when it is partially or fully submerged as the sub-compartments help reduce the potential adverse effects of culture liquid agglomeration and large gas bubbles as will be discussed more in detail herein.

The sub-compartments may be sealed from each other. If the sub-compartments are sealed from each other, the sub-compartments will act as an array of smaller photobioreactors. This will further reduce problems with agglomeration and large gas bubbles when the photobioreactor is submerged.

The sub-compartments may also be connected to allow limited liquid and/or gas transport between the sub-compartments. This will reduce problems with agglomeration and large gas bubbles when the photobioreactor is submerged, while retaining the flexibility of the photobioreactor and the advantage of common distribution of $CO_2$ and other nutrients to the culture liquid and removal of oxygen from the reactor.

The photobioreactor may further comprise means for temporarily dividing the algae compartment of the photobioreactor into two or more sub-compartments. Temporarily dividing the algae compartment of the photobioreactor allows the combined benefits of having an unrestricted flat panel structure when the photobioreactor is floating on a water surface and a sub-compartment structure when the photobioreactor is in a partially or fully submerged position. The photobioreactor or the algae compartment thereof, when floating on the surface of the surrounding water will generally comprise at least a flexible top sheet facing the atmosphere, and a flexible bottom sheet facing the water, between which two sheets the algae culture is maintained. The means for temporarily dividing the algae compartment of the photobioreactor may for example comprise a member adapted for pressing a top sheet of the photobioreactor towards a bottom sheet of the photobioreactor such that a sub-compartment is formed inside the photobioreactor on each side of the depression. In an embodiment, said means for dividing the algae compartment of the photobioreactor into two or more sub-compartments comprises at least one elongated member, such as a rope, a cable or a rod stretched above the photobioreactor and arranged to be brought down to press the top sheet of the photobioreactor towards the bottom sheet of the photobioreactor such that a sub-compartment is formed inside the photobioreactor on each side of said at least one elongated member.

In another embodiment, said means for dividing the photobioreactor into two or more sub-compartments comprises at least one additional compartment or tube, separate from the algae compartment and arranged in contact with the top sheet of the photobioreactor and adapted to be filled with a liquid having higher density than the culture liquid, such that when the additional compartment or tube is filled with the high density liquid, the filled compartment or tube is capable of pressing the top sheet of the photobioreactor towards the bottom sheet of the photobioreactor such that a sub-compartment is formed inside the algae compartment of the photobioreactor on each side of said filled compartment.

DETAILED DESCRIPTION OF PREFERRED EMBODIMENTS OF THE INVENTION

Non-limiting examples of the realization of the invention can be found in the attached drawings and is described further in the following text. The terms culture liquid and culture medium are used interchangeably herein and may refer to the entire algae culture, i.e. the mixture of algae and the aqueous medium in which the algae are suspended, or simply to the aqueous medium used for suspending the algae.

Figure 1A:
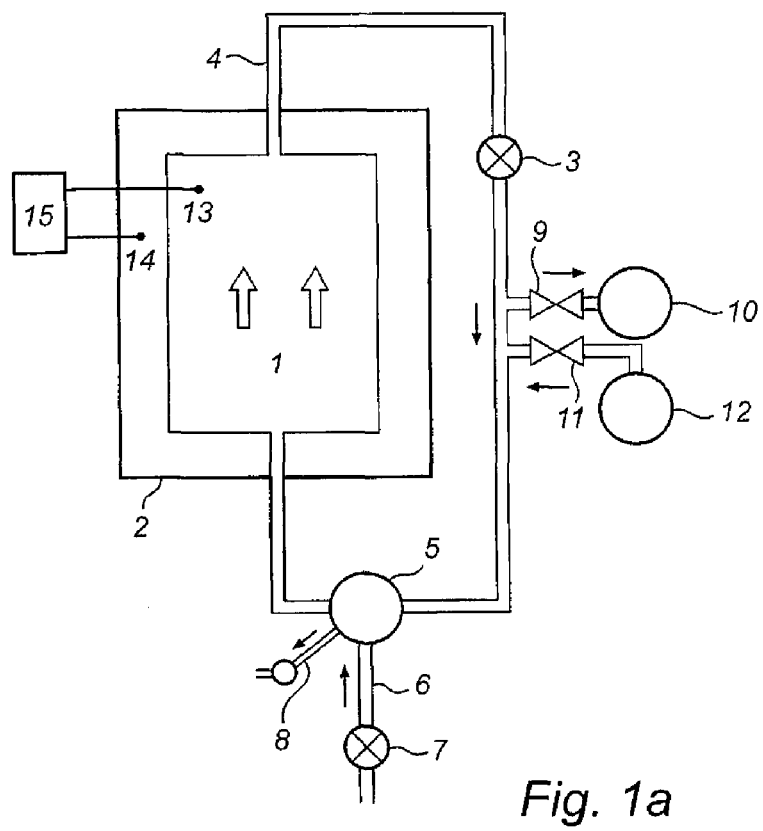
FIG. 1a is a schematic view of a photobioreactor system.

FIG. 1a is a view of a complete photobioreactor system. The panel shaped photobioreactor 1 (also referred to herein as the "reactor") floats on a water body, here an artificial pond 2. The size of such a photobioreactor 1 can vary, a length of 50 meters and a breadth of about 10 meters could be a possible realization. The photobioreactor 1 is manufactured from a flexible transparent material and within the photobioreactor is the culture liquid, in which the algae are suspended. By solar radiation on the photobioreactor 1, the algae are enabled to produce biomass via photosynthesis. Carbon dioxide is used during this process and oxygen is produced. Therefore the culture medium is always moving while illuminated, in order to provide new carbon dioxide and to remove oxygen which can be toxic for the algae. The culture medium will be moved via a pump 3. The culture medium is thus moving through the photobioreactor and is brought back via a tube 4. The gas exchange will take place in a tank 5, to which a tube system 6 will steadily provide a carbon dioxide rich gas mixture by means of a compressor 7. The carbon dioxide rich gas mixture can have its origin for instance from an electrical power plant using fossil fuels. The degassed oxygen will be lead out via a tube 8 equipped with a sterile filter. Culture liquid with algae biomass can be taken out of the system via a valve 9 and be stored in a tank 10 until this harvested volume is processed further. New medium is provided to the system via a further valve 11 from a storage tank 12. This serves to level out the loss of liquid caused by the harvest and to supply culture liquid with new nutrients.

In an alternative embodiment (not shown), carbon dioxide is provided to the growing algae from a tube or hose located in the reactor, the tube or hose having one or more outlet(s) for carbon dioxide. Thus, in this embodiment the cultivation liquid must not move to pass tank 5 in order to be supplied with carbon dioxide.

Sensors 13 for determination of the salinity and the temperature of the culture liquid, and sensors 14 for determination of the salinity and the temperature of the surrounding water, are connected to a control unit 15. The control unit 15 determines the density difference between the culture liquid and the surrounding water, based on information from sensors 13, 14 as well as other parameters and stored data. The control unit controls pumps (not shown) supplying seawater and fresh water, respectively, to the pond 2. In another embodiment (not shown), the control unit 15 controls means for changing the salinity of the culture liquid in the photobioreactor 1.

Figure 1B:
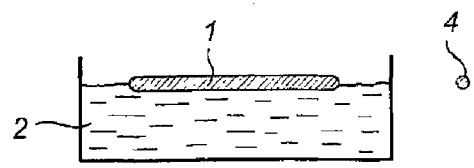
FIG. 1b is a cross-sectional view of a photobioreactor system.

FIG. 1b shows a cross section through such a system. The photobioreactor 1 is cut in a lateral way, in this figure the photobioreactor floats on a water body 2. The vertical thickness of the culture liquid in the photobioreactor is typically between 1 and 30 cm. The depth of the water body 2 might vary significantly. The tube 4 which is used to circulate the culture liquid is seen in the lateral cut as well.

The Culture Liquid of the Photobioreactor

The algae culture rests in culture liquid in the photobioreactor. The culture liquid is an aqueous solution comprising different salts and other nutrients, e.g. carbon sources such as $CO_2$, glucose or succinate, so that the algae can produce biomass or specific molecules. The specific nutrient content of the culture liquid may vary depending on the type of algae cultured in the photobioreactor or on the different molecules the algae culture is supposed to produce. The culture liquid in the photobioreactor may be replaced by pumping fresh culture liquid through the photobioreactor at any flowrate, so that the algae culture is provided with fresh nutrients. If the culture liquid is pumped through the photobioreactor, the flow rate at which the culture liquid is pumped is preferably adjusted so as to minimize any loss of algae from the photobioreactor. The temperature of the culture liquid in the photobioreactor and the surrounding water is continuously measured. The measured temperature is compared to predetermined temperature values, which may be temperatures within a temperature interval in which the conditions for the algae culture is optimal, e.g. a temperature interval that promotes the highest growth rate of the algae culture or the highest production rate of a specific molecule.

Supplying $CO_2$ to the Culture Liquid of the Photobioreactor

Algae require for their growth large amounts of $CO_2$ since they use this as a key source of carbon. Furthermore, in the process of photosynthesis, oxygen is produced, which might be toxic to the algae. The mass transfer of these gases across the liquid-gas barrier is therefore crucial for high productivity. A number of possible ways of providing $CO_2$ to the algae culture, and for removing formed oxygen from the same will be described hereinbelow. The methods described herein should not be construed as limiting to the present invention. Other methods that may also be apparent to a person skilled in the art in the light of the present disclosure are also considered to be within the scope of the present invention.

In an embodiment (not shown), mass transfer of $CO_2$ to the culture medium is achieved via passive diffusion of gaseous $CO_2$ over a large surface area of the culture medium. Assuming that the kinetics of diffusion processes as described by Fick's first and second law and the subsequent hydration and deprotonization processes are fast enough to provide the algae culture with enough $CO_2$ and to avoid toxic effects of $O_2$ via photo-oxidation, a passive diffusion of $CO_2$ via a large surface would be sufficient. Passive diffusion has the advantage that no energy is needed to move water or to force $CO_2$ into the water. Additionally, investment costs will be reduced since no active aeration would be required. In such a case, $CO_2$ transfer will take place at the interfacial layer between water and the $CO_2$ gas without any more energy added. In a more specific embodiment this could be realized by generating a gas bubble of $CO_2$ rich gas above the culture medium inside the photobioreactor.

In another embodiment (not shown), $CO_2$ is bubbled through the culture medium. The gaseous $CO_2$ may preferably be supplied by a tube or a tube-like device, extending into the culture medium. Such a system could comprise holes, through which a $CO_2$ rich gas may be pushed by applying pressure from an external device. The tubes or tube like devices may for example be fixed at the bottom of the reactor and the typical direction of the holes would be into the direction of the water surface.

During operation of the photobioreactor, the $CO_2$ rich gas may be supplied continuously to the culture medium. This embodiment also has the additional advantage that it leads to a continuous degassing of oxygen close to statu nascendi, i.e. the oxygen produced is removed from the culture medium shortly after it is formed.

Alternatively, the $CO_2$ rich gas can be added in short pulses. Various means exist to determine the length of a pulse, the amount of gas pushed in, the pressure the gas is pushed and the time between pulses. In an embodiment the gas could be pulsed by a timer, which gives a regular signal, e.g. every 5 minutes for a pulse of 1 minute. In another embodiment, the pulse is controlled by a special unit which is capable of estimating the amount of $CO_2$ used by the algae and calculating the optimal length of the pulse, the amount of gas to be pushed in, the pressure the gas is to be pushed in with, and the time between the pulses. To estimate the amount of $CO_2$ required, the unit may comprise different sensors, e.g. a sensor measuring the light intensity, a sensor measuring the temperature and a sensor measuring the biomass density in the photobioreactor. Using the data points received by these sensors a process controller would calculate the optimal pulse pattern for the photobioreactor system.

The amount of added $CO_2$ may also be related to the pH in the reactor. A pH electrode is arranged in the culture medium, and this electrode continuously measures the voltage across a semi-permeable membrane allowing protons to pass the membrane against a defined redox-system, e.g. against an Ag/AgCl electrode. The voltage is registered by a process control unit. The process control unit will add a $CO_2$ pulse as soon as the voltage reaches a predefined point. The parameters of the pulse, such as time, amount of pulses per minutes, voltage to stop the pulsing can be entered into the process control unit.

Figure 2A:
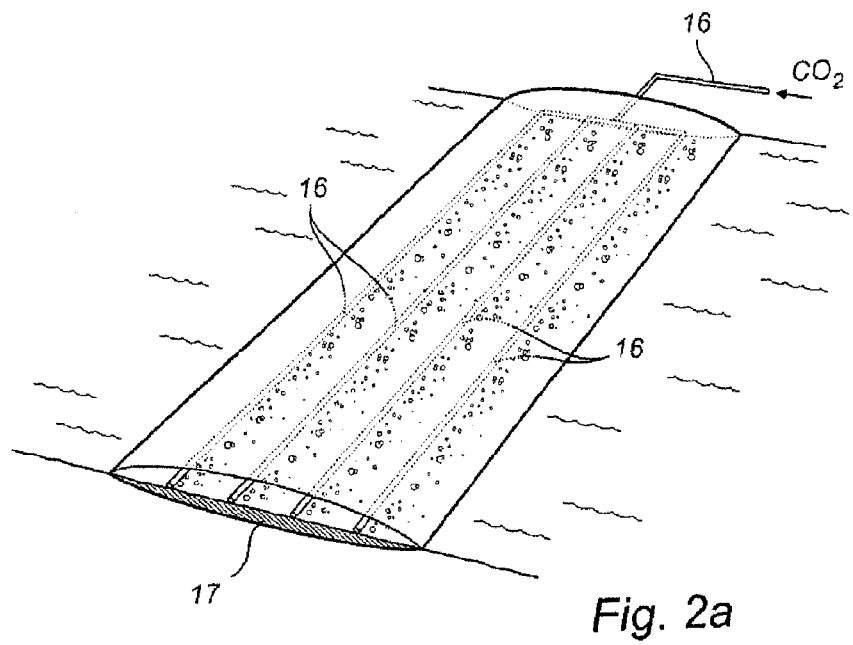
FIG. 2a shows a three-dimensional view of a photobioreactor with a $CO_2$ supply tube floating on the culture liquid compartment due to its low density.
Figure 2B:
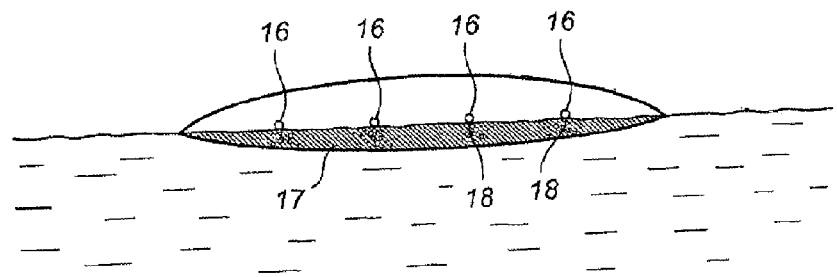
FIG. 2b displays a vertical cross-section of a photobioreactor with a $CO_2$ supply tube floating on the culture liquid due to its low density.

In another embodiment, shown in FIGS. 2a and 2b, gaseous $CO_2$ may be supplied to the culture medium by a tube or a tube-like device extending into the photobioreactor and arranged to float on top of the surface of the culture medium due to its lower density. Bubbling of gaseous $CO_2$ is performed similarly as in the case described above, wherein the tube or tube-like device extends into the culture medium. However, the tube or tube-like device through which the $CO_2$ is supplied will be specifically designed to float on the surface of the culture medium in the photobioreactor. This is achieved by the density of the whole (16) aeration system being lower than the density of the algae culture medium (17). The holes (18) in the tube or tube-like device, through which the $CO_2$ is pushed into the culture medium may preferably point downwards in this embodiment to achieve the best possible gas transfer. The holes will thereby be positioned at, or slightly below, the surface of the culture medium.

During operation of the photobioreactor, the $CO_2$ rich gas may be supplied continuously to the culture medium. This embodiment also has the additional advantage that it leads to a continuous degassing of oxygen close to statu nascendi, i.e. the oxygen produced is removed from the culture medium shortly after it is formed.

Alternatively, the $CO_2$ rich gas can be added in short pulses. Various means exist to determine the length of a pulse, the amount of gas pushed in, the pressure with which the gas is pushed in and the time between pulses. In an embodiment the gas could be pulsed by a timer, which gives a regular signal, e.g. every 5 minutes for a pulse of 1 minute. In another embodiment, the pulse is controlled by a special unit which is capable of estimating the amount of $CO_2$ used by the algae and calculating the optimal length of the pulse, the amount of gas to be pushed in, the pressure the gas is to be pushed in with, and the time between the pulses. To estimate the amount of $CO_2$ required, the unit may comprise different sensors, e.g. a sensor measuring the light intensity, a sensor measuring the temperature and a sensor measuring the biomass density in the photobioreactor. Using the data points received by these sensors a process controller would calculate the optimal pulse pattern for the photobioreactor system.

The amount of added $CO_2$ may also be related to the pH in the reactor. A pH electrode is arranged in the culture medium, and this electrode continuously measures the voltage across a semi-permeable membrane allowing protons to pass the membrane against a defined redox-system, e.g. against an Ag/AgCl electrode. The voltage is registered by a process control unit. The process control unit will add a $CO_2$ pulse as soon as the voltage reaches a predefined point. The parameters of the pulse, such as time, amount of pulses per minutes, voltage to stop the pulsing can be entered into the process control unit.

$CO_2$ does not necessarily have to be supplied to the culture medium in the form of gaseous $CO_2$ inside the photobioreactor. The $CO_2$ enriched medium may also be prepared outside the photobioreactor, e.g. by bubbling gaseous $CO_2$ through an aqueous medium. In other words, instead of supplying the $CO_2$ in the transparent part of the photobioreactor this could be done outside of the actual photobioreactor. In an embodiment, such a system may employ a vertical tank containing an aqueous medium wherein $CO_2$ rich gas is supplied at the bottom or close to the bottom of the tank. While bubbles of $CO_2$ rise up through the aqueous medium, $CO_2$ will transfer from the bubbles into the aqueous medium, and at the same time the oxygen may be removed from the culture medium. In a preferred embodiment, the aqueous medium which is enriched with $CO_2$ is culture medium from the photobioreactor which is enriched with $CO_2$ and subsequently returned into the photobioreactor. As the tank may have a height of several meters the residential time of $CO_2$ may be comparatively long, allowing for a good mass transfer. To bubble $CO_2$ into a vertical tank, energy is required to work for instance against the hydrostatic pressure. The energy, which is put in for pressurizing the gas, may also be used to move the aqueous medium from the algae compartment into the $CO_2$ enrichment device and back to the algae compartment.

In another embodiment, instead of bubbling $CO_2$ through the algae culture medium inside or outside of the photobioreactor, the $CO_2$ supply is facilitated by the use of a semi-permeable membrane. The use of such a membrane would have various advantages compared to the bubbling:

a) Such a membrane would work as a one-way-valve, meaning that the membrane would allow $CO_2$ to enter the culture medium, but prevent water from entering into the $CO_2$ supply system, as such a membrane would be permeable for $CO_2$ but not for water.

b) Lower energy consumption. Since no bubble generation is required, the membrane method allows $CO_2$ supply with lower energy consumption compared to the bubbling process.

c) Low shear-stress. By avoiding the bubbling, the shear-stress on the algae cells is reduced. Less shear stress on the algae results in less dead algae cells in the algae culture medium and therefore less organic material which is prone to decomposition which may reduce the efficiency of the photobioreactor. Furthermore, this would significantly reduce the risk of contamination by heterotrophic organisms.

d) Increased mass transfer rate. The use of a membrane allows a higher $CO_2$ pressure than the embodiment employing passive diffusion described above, since the $CO_2$ pressure against the membrane is not limited to the surrounding atmospheric air pressure as it would be the case of passive diffusion. Furthermore, the membrane might have a higher surface area than a flat surface, such as the surface of the culture medium, with the same size as the membrane.

The mass transfer of $CO_2$ and/or oxygen may also be facilitated by moving the photobioreactor, e.g. by tilting the reactor.

The Photobioreactor in a Closed Body of Water

The term "closed body of water" refers to well-defined systems of water allowing control of, e.g., the amount or type, such as fresh, brackish or salt, of water therein. Examples of closed bodies of water are natural or artificial ponds or pools.

In one embodiment, the photobioreactor rests on the surface of a closed body of sea water, i.e. salt water, as a starting position. When the photobioreactor rests, or floats, on the surface of a body of sea water, the density of the photobioreactor is lower compared to the density of the body of sea water. If the position of the photobioreactor needs to be lowered, the density difference between the photobioreactor and the body of sea water is regulated. As an example, the position of the photobioreactor may need to be lowered when the measured temperature of the culture liquid is higher or expected to be higher than a predetermined temperature value. To regulate the density difference between the photobioreactor and the body of sea water, the salinity of the body of sea water is decreased. This is achieved by replacing the sea water with fresh water. As the sea water is replaced by fresh water, the salinity of the closed body of water gradually decreases, i.e. the density of the water surrounding the photobioreactor decreases. As an alternative, the sea water may be replaced with brackish water. The density of the culture liquid, the overall density of the photobioreactor as well as the density of the surrounding water are continuously measured so that the density difference between the photobioreactor and the surrounding water is continuously determined. The photobioreactor sinks in the closed body of water due to its higher density compared to the surrounding water and the position of the photobioreactor is lowered. The position of the photobioreactor may be lowered until the measured temperature of the culture liquid is within desirable temperature range.

In another embodiment, the photobioreactor rests on the surface of a closed body of fresh water as a starting position. When the photobioreactor rests, or floats, on the surface of a body of fresh water, the density of the photobioreactor is lower compared to the density of the body of fresh water. If the position of the photobioreactor needs to be lowered, the density difference between the photobioreactor and the body of fresh water is regulated. As an example, the position of the photobioreactor may need to be lowered when the measured temperature of the culture liquid is higher or expected to be higher than a predetermined temperature value. To regulate the density difference between the photobioreactor and the body of fresh water, the salinity of the culture liquid is increased. This is achieved by replacing or complementing the culture liquid by culture liquid of higher salinity, i.e. by pumping culture liquid of higher salinity into the photobioreactor. The flow rate of the culture liquid is set so as to allow the algae to adapt to the higher salt concentrations in the culture liquid and to minimize any loss of algae in the photobioreactor. As the culture liquid is replaced or complemented by culture liquid of higher salinity, the density of the photobioreactor increases. The density of the culture liquid, the overall density of the photobioreactor as well as the density of the surrounding water are continuously measured so that the density difference between the photobioreactor and the surrounding water is continuously determined. The photobioreactor sinks in the closed body of water due to its higher density compared to the surrounding water and the position of the photobioreactor is lowered. The position of the photobioreactor may be lowered until the measured temperature of the culture liquid is within desirable temperature range.

In another embodiment, the photobioreactor rests below the surface of a closed body of sea water, i.e. salt water, as a starting position. When the photobioreactor is below the surface of a body of sea water, the density of the photobioreactor is higher compared to the density of the body of sea water. If the position of the photobioreactor needs to be raised, the density difference between the photobioreactor and the body of sea water is regulated. As an example, the position of the photobioreactor may need to be raised when the measured temperature of the culture liquid is lower or expected to be lower than a predetermined temperature value. To regulate the density difference between the photobioreactor and the body of sea water, the salinity of the culture liquid is decreased. This is achieved by replacing or complementing the culture liquid with culture liquid of lower salinity, i.e. by pumping culture liquid of lower salinity into the photobioreactor. The flow rate of the culture liquid is set so as to allow the algae to adapt to the lower salt concentrations in the culture liquid and to minimize any loss of algae in the photobioreactor. As the culture liquid is replaced or complemented by culture liquid of lower salinity, the density of the photobioreactor decreases. The density of the culture liquid, the overall density of the photobioreactor as well as the density of the surrounding water are continuously measured so that the density difference between the photobioreactor and the surrounding water is continuously determined. The position of the photobioreactor is raised in the closed body of water due to its lower density compared to the surrounding water. Raising the photobioreactor in the body of water may continue until the measured temperature of the culture liquid is within a desirable temperature range.

In another embodiment, the photobioreactor rests below the surface of a closed body of fresh water as a starting position. When the photobioreactor is below the surface of a body of fresh water, the density of the photobioreactor is higher compared to the density of the body of fresh water. If the position of the photobioreactor needs to be raised, the density difference between the photobioreactor and the body of fresh water is regulated. As an example, the position of the photobioreactor may need to be raised when the measured temperature of the culture liquid is lower or expected to be lower than a predetermined temperature value. To regulate the density difference between the photobioreactor and the surrounding body of fresh water, the salinity of the surrounding water is increased. This is achieved by replacing the fresh water with sea water, i.e. salt water. As the fresh water is replaced by sea water, the salinity of the closed body of water gradually increases, i.e. the density of the water surrounding the photobioreactor increases. The density of the culture liquid, the overall density of the photobioreactor as well as the density of the surrounding water are continuously measured so that the density difference between the photobioreactor and the surrounding water is continuously determined. The position of the photobioreactor is raised in the closed body of water due to its lower density compared to the surrounding water. Raising the photobioreactor in the body of water may continue until the measured temperature of the culture liquid is within a desirable temperature range.

In one embodiment, particularly when the photobioreactor is in a closed body of water, density of the culture liquid and density of the surrounding water are changed simultaneously.

Thus, the salinity of the surrounding water is simultaneously decreased as the salinity of the culture liquid is increased, or the salinity of the surrounding water is simultaneously increased as the salinity of the culture liquid is decreased. Simultaneous regulation of the salinity of the, preferably closed, body of water and the culture liquid increases the speed at which the density difference between the photobioreactor and the surrounding water is regulated, thereby increasing the speed at which the photobioreactor is lowered or raised in the surrounding water.

In one embodiment, particularly when the photobioreactor is in a closed body of water, the temperature of the body of water is used as an additional means for providing a desirable density difference, i.e. the temperature is regulated as a complement or an alternative to regulating the salinity of the culture liquid or the water surrounding the reactor. When the position of the photobioreactor needs to be lowered, the temperature of the closed body of water is increased, thereby decreasing the density of the surrounding water. Further, when the position of the photobioreactor needs to be raised, the temperature of the closed body of water is decreased, thereby increasing the density of the surrounding water. Thus, regulating the temperature of the water surrounding the reactor influences the speed at which the photobioreactor is lowered or raised in the surrounding water.

In an embodiment where the photobioreactor rests on the surface of a closed body of sea water, i.e. salt water, as a starting position, other additives than fresh water are added to the surrounding water in order to decrease the density of the medium surrounding the reactor. For example, a non-aqueous liquid of lower density than water is added to the closed body of water so as to decrease the density of the medium surrounding the reactor.

In an embodiment where the photobioreactor rests below the surface of a closed body of fresh water as a starting position, other additives than sea water, i.e. salt water, are added to the closed body of fresh water in order to increase the density of the medium surrounding the reactor. For example, a non-aqueous liquid of higher density than water is added to the closed body of water so as to increase the density of the medium surrounding the reactor.

The Closed Photobioreactor in Open Water

The term "open water" refers to natural bodies of water, such as lakes, rivers or the sea, wherein an effective control of the chemical or physical properties of the water is difficult or impossible.

In one embodiment, the photobioreactor rests on the surface of open fresh water as a starting position. When the photobioreactor rests, or floats, on the surface of open fresh water, the density of the photobioreactor is lower compared to the density of the fresh water. If the position of the photobioreactor needs to be lowered, the density difference between the photobioreactor and the open fresh water is regulated. As an example, the position of the photobioreactor may need to be lowered when the measured temperature of the culture liquid is higher or expected to be higher than a predetermined temperature value. To regulate the density difference between the photobioreactor and the surrounding water, the salinity of the culture liquid is increased. This is achieved by replacing or complementing the culture liquid by culture liquid of higher salinity, i.e. by pumping culture liquid of higher salinity into the photobioreactor. The flow rate of the culture liquid is set so as to allow the algae to adapt to the higher salt concentrations in the culture liquid and to minimize any loss of algae in the photobioreactor. As the culture liquid is replaced or complemented by culture liquid of higher salinity, the density of the photobioreactor increases. The density of the culture liquid, the overall density of the photobioreactor as well as the density of the open fresh water are continuously measured so that the density difference between the photobioreactor and the surrounding water is continuously determined. The photobioreactor sinks in the open fresh water due to its higher density compared to the surrounding water and the position of the photobioreactor is lowered. The position of the photobioreactor may be lowered until the measured temperature of the culture liquid is within a desirable temperature range.

In another embodiment, the photobioreactor rests below the surface of open sea water, i.e. salt water, as a starting position. When the photobioreactor is below the surface of the open sea water, the density of the photobioreactor is higher compared to the sea water. If the position of the photobioreactor needs to be raised, the density difference between the photobioreactor and the sea water is regulated. As an example, the position of the photobioreactor may need to be raised when the measured temperature of the culture liquid is lower or expected to be lower than a predetermined temperature value. To regulate the density difference between the photobioreactor and the sea water, the salinity of the culture liquid is decreased. This is achieved by replacing the culture liquid by culture liquid of lower salinity, i.e. by pumping culture liquid of lower salinity into the photobioreactor. The flow rate of the culture liquid is set so as to allow the algae to adapt to the lower salt concentrations in the culture liquid and to minimize any loss of algae in the photobioreactor. As the culture liquid is replaced by culture liquid of lower salinity, the density of the photobioreactor decreases. The density of the culture liquid, the overall density of the photobioreactor as well as the density of the sea water are continuously measured so that the density difference between the photobioreactor and the surrounding water is continuously determined. The position of the photobioreactor is raised in the sea water due to its lower density compared to the surrounding water. Raising the photobioreactor in the sea water may continue until the measured temperature of the culture liquid is within a desirable temperature range.

Control System

In one embodiment, the salinity of the culture liquid, and thus indirectly the position of the photobioreactor, is regulated by a multi-purpose system. This system is programmed with information related to the photobioreactor, such as the overall weight and density of the photobioreactor and the amount of biomass and culture liquid that is contained in the photobioreactor. Moreover, the system continuously measures the temperature, salinity and density of the culture liquid and the density of the surrounding water, thereby continuously determining the density difference between the photobioreactor and the surrounding water. The system also controls the concentration of the different components of the culture liquid, such as the salt concentration. The system may then automatically regulate the position of the photobioreactor in the surrounding water as a response to a change in the temperature of the culture liquid, so as to keep the algae culture at a constant temperature. The system may thus be equipped with known control circuits or algorithms, such as control algorithms with feedback mechanisms, to allow optimal stability when regulating the position of the photobioreactor.

In a further embodiment, when the photobioreactor is in a closed body of water, the salinity and temperature of the surrounding water is regulated by the multi-purpose system described above. In an embodiment of the photobioreactor having additional compartments or tubes, the control system also regulates the filling and emptying of gas, water and other liquids of the compartments or tubes. In one embodiment, the multi-purpose system controls not only parameters related to positioning of the photobioreactor but also parameters relevant to growth of the algae. Thus, the control system also measures and regulates $O_2$ and $CO_2$ contents of the algae culture.

Additional Means for Controlling the Position and/or Shape of the Photobioreactor The vertical position and/or the shape of the photobioreactor according to the present invention may be controlled by providing a suitable density difference between the culture liquid and the surrounding water in which the reactor is suspended. However, sometimes additional means for controlling the position and/or shape of the photobioreactor may be useful. This may for instance be the case when the photobioreactor needs to be submerged quickly. Such means may include additional compartments or tubes capable of being filled with high or low density medium in order to assist submersion or floatation of the photobioreactor, mechanical means for assisting submersion or floatation of the photobioreactor, and sub-compartments within the algae compartment of the photobioreactor for controlling the shape of the reactor when it is submerged. These three types of means will be discussed in detail hereinbelow.

Additional Compartments or Tubes Capable of being Filled with High or Low Density Medium In one embodiment, the photobioreactor is equipped with additional compartments or tubes providing means to increase the speed at which the position of the photobioreactor is changed. The compartments or tubes may contain gas, water or any other liquid. When the photobioreactor rests on a water surface, the compartments or tubes may contain only gas. If the position of the photobioreactor needs to be lowered, the compartments or tubes are filled with water or a liquid of high density, thereby increasing the overall density of the photobioreactor. When the photobioreactor is below the surface of the water and the position of the photobioreactor needs to be raised, the water or the liquid of high density in the compartments or tubes is pushed out and replaced with gas, thereby decreasing the overall density of the photobioreactor. Thus, the additional compartments or tubes increase the speed at which the density difference between the photobioreactor and the surrounding water is regulated. The additional compartments or tubes may therefore be used when the position of the photobioreactor needs to be adapted quickly, such as in response to short-term changes of the temperature of the culture liquid. By "short-term changes" is referred to changes on the minute or hour scale. The additional compartments or tubes could be arranged anywhere on the photobioreactor. The additional compartments or tubes may be of the same material as the rest of the photobioreactor or of a different material, which is more rigid and potentially also more durable. The additional compartments or tubes may also comprise a system of several tubes in liquid connection with each other or they may comprise a wider compartment having inner gluing or welding points or connections done by similar techniques to provide structural stability.

Figure 3:
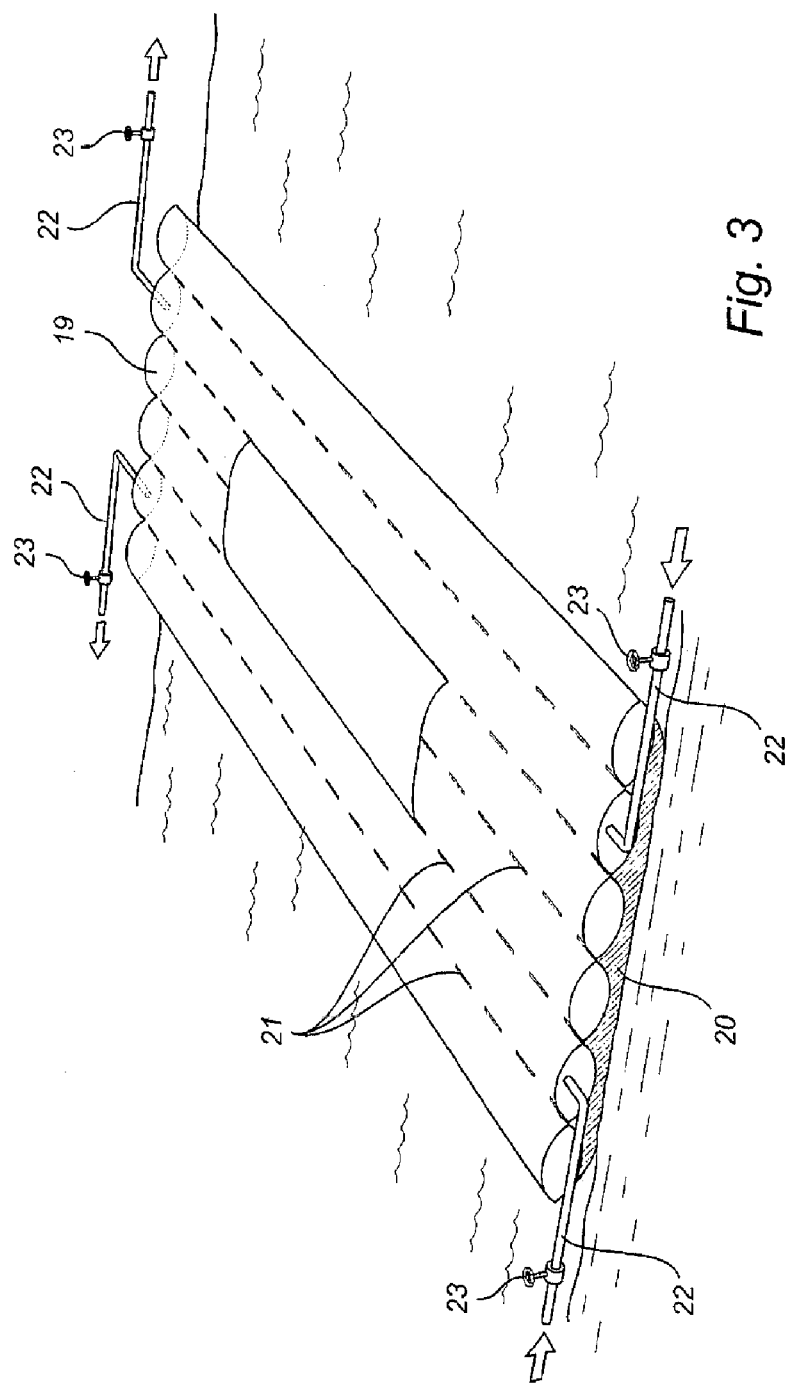
FIG. 3 shows a photobioreactor with an additional compartment for controlling vertical position and or the shape of the reactor.

In an embodiment shown in FIG. 3, an additional compartment is arranged on top of the photobioreactor. In this embodiment, the density of the total reactor system can be changed by adding a liquid with high density, preferably salt water, in the additional compartment (19), which is separate from the algae compartment (20). The compartment, when filled, would increase the density of the whole reactor system such that the sinking process is accelerated. In this embodiment, the additional compartment is arranged on top of the photobioreactor. The additional compartment comprises inner gluing points (21) to provide structural stability. The additional compartments or tubes may be connected to a supply of high density liquid by one or more hoses (22) provided with valves (23) at one side of the reactor and a similar connection at the opposite side of the reactor. When used for accelerating the submersion of the photobioreactor according to this embodiment, the additional compartment will be filled with water from one side and the valves at the other side will also be opened. By starting the filling process from one side this side will become submerged first. Remaining air in the additional compartment may thereby be collected at one side of the photobioreactor and be pushed out more efficiently. The filling process will be continued until all air is out and the complete reactor starts to sink. The valves opposite to the filling hoses are then closed. The filling process may be stopped at this point or the filling process may be continued for a while. Continuing the filling process increases the pressure in the additional compartment, thus increasing the rigidity of this compartment and allowing it to provide additional structural stability to the photobioreactor during submersion and in a partially or fully submerged mode.

When the reactor system should go up, the salt water of the additional compartment will be pumped out by a pump, having the valves opposite to the pump closed to avoid that air bubbles enter the new compartment. To accelerate the process of going up, the valves opposite to the pump will be opened and through the respective hoses pressurized air or flue gases will be pushed in.

Mechanical Means for Assisting Submersion or Floatation of the Photobioreactor

The photobioreactor may be equipped with mechanical means for accelerating submersion or floatation when the position of the photobioreactor needs to be adapted quickly, e.g. for optimizing the growth conditions of the algae, e.g. the temperature, or due to weather related conditions such as strong winds. Such mechanical means may e.g. comprise a net or at least one elongated member, such as a rope, cable or rod, stretched above the photobioreactor and arranged to be brought down or up to assist the submersion or floatation of the photobioreactor. Generally it will be useful to have two or more elongated members arranged in parallel and distributed at suitable distances across the length of the photobioreactor. The elongated members may be brought down or up simultaneously or in sequence, e.g. such that the entire photobioreactor is submerged simultaneously, or such that one side of the reactor is submerged first and the other side of the reactor is submerged subsequently.

Figure 4A:
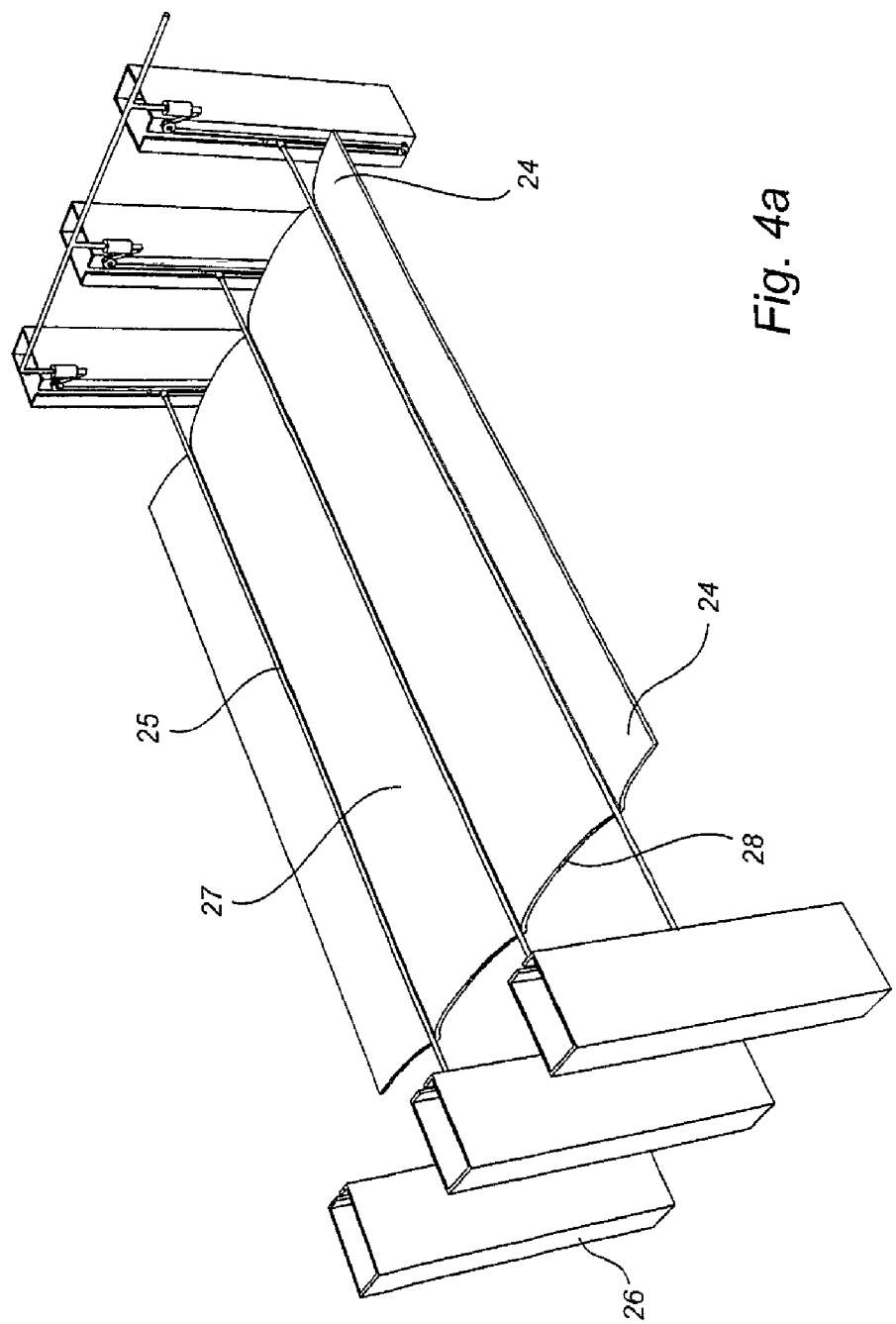
FIG. 4a is a schematic view of a photobioreactor with ropes for creating temporary sub-compartments and for accelerating the submersion process.
Figure 4B:
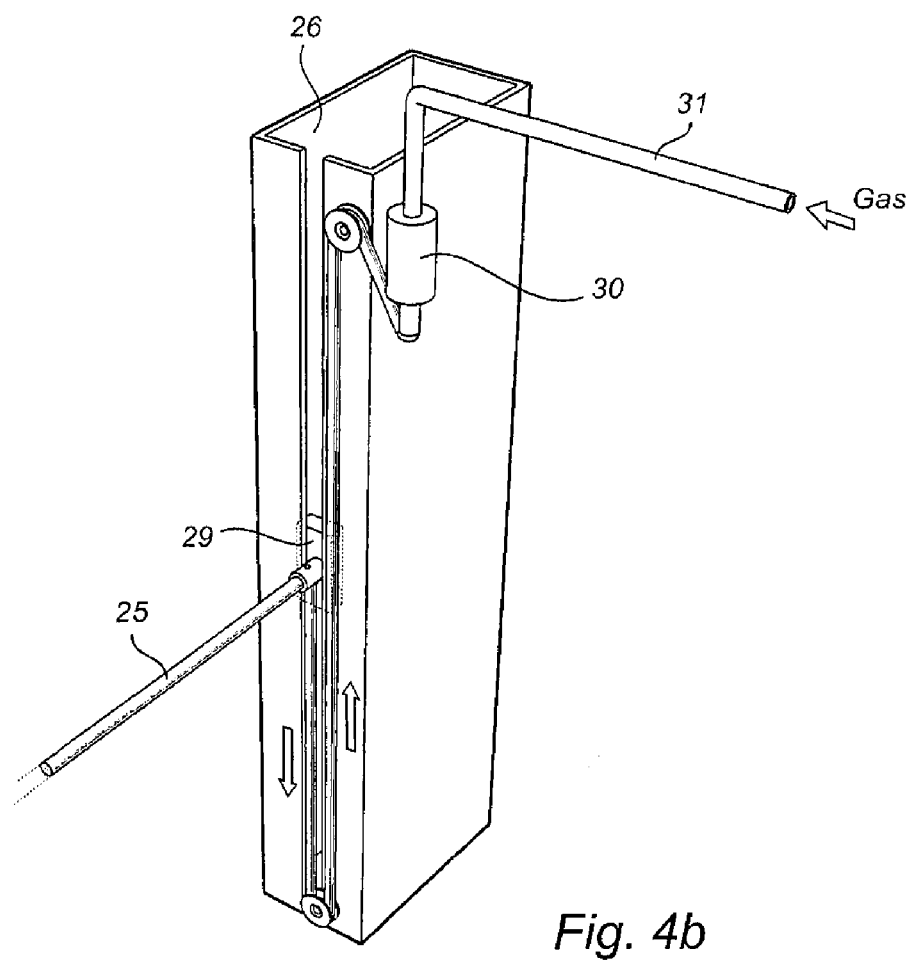
FIG. 4b is a magnification from FIG. 4a of a vertical profile with a rail to guide the reactor movement.

A specific embodiment is depicted in FIG. 4a. Above the bioreactor (24) there are in regular distances ropes (25) installed, this could be done in a distance of for example every 1-2 meters. The ropes have minimum the length of the size of reactor and at both ends they are connected to vertical profiles (26). When the photobioreactor is to be submerged, the ropes are pulled down at the vertical profiles on each side of the reactor respectively, such that the reactor (27) is pushed down by the ropes. Various arrangements may be used in order to fix and move the ropes. In one specific embodiment, as shown in FIG. 4b, the ropes could be fixed to a T-like structure (29), which is vertically movable along a plastic or metal profile. The plastic or metal profile is vertically fixed to the ground and contains a rail where the movable structure can be moved up and down. The rope is fixed to the movable structure. To move the structure, energy and a mechanical system is required. The mechanical system could be a piston (30) at each of the profiles or one central piston could supply the mechanical force for several profiles. Each piston could be powered by pressurized gas (31). The pressurized gas may e.g. be provided by a gas tube, a compressor, or it may be pressurized $CO_2$ rich gas from an emitter, e.g. a power plant. The $CO_2$ source may preferably be the same used to for providing $CO_2$ to the culture liquid.

In an embodiment with two or more ropes, the movement of the ropes can be performed in various ways. All ropes may be moved down with the same speed, such that the entire photobioreactor is brought down simultaneously. However, it has been found that it is often advantageous to move down first the ropes on one side of the reactor thereby bringing the reactor at this side down first, and subsequently moving down the other side as well. Such a stepwise procedure has several advantages. If one side of the reactor is moved down first, then all the gas trapped inside the reactor will move to the other side. In such a system the gas outlets could be arranged specifically at this other side. This arrangement allows the excess gas to be pushed out by the movement of the reactor. This may be advantageous compared to the case where the entire photobioreactor is brought down simultaneously, whereby gas bubbles or agglomerates may occur at random positions within the reactor. According to the same principle all the culture medium would collect in a given place and the control of the position of the culture medium would make the potential later partitioning easier. Furthermore, the harvesting procedure is facilitated as all the biomass is agglomerated at one side of the reactor. Finally, bringing the reactor down at one side first requires less force and allows the surrounding water to flow around the reactor in a more controlled fashion, creating less turbulence, which could make this process more stable compared to a process where the entire reactor is brought down simultaneously. Since the photobioreactor is very flexible, and may be adversely affected by turbulence and rapidly moving water, this is an important advantage.

The additional compartments or tubes, as well as the mechanical means described above may, besides accelerating submersion or floatation, provide the additional advantage of stabilizing the physical shape of the photobioreactor during submersion and in a partially or fully submerged mode.

Sub-Compartments

Since the photobioreactor of the present invention is very flexible, the shape of the reactor may be influenced by internal and external impacts and inhomogenities. Hence, in order to retain the shape and optimal function of the photobioreactor the control of such impacts and inhomogenities may be important. Therefore a number of embodiments of the present invention are described hereinbelow, which deal with different aspects of operation of the inventive photobioreactor.

By using a thin and flexible reactor material, the reactor forms a perfect flat and homogenous system when it is floating on an expanse of water. There are, however, two major forces, which could contribute to destabilizing the reactor system. a) The shape and behavior of the photobioreactor may be affected by the formation of large gas bubbles inside the photobioreactor. Bubbling of gaseous $CO_2$ through the culture medium may be desired to supply enough $CO_2$ to support an optimal growth rate of the algae culture. Constant inflow of gas into the photobioreactor might lead to the formation of one or more large gas bubbles above the culture liquid. In order to control the gas bubbles, various solutions may be considered. One or more gas outlets may be connected to the photobioreactor. The number and positions of outlets as well as the inner diameter of the outlets are important factors influencing the size of the bubble. Another method of controlling the size and behavior of the gas bubbles is by dividing the photobioreactor into smaller sub-compartments. This may be achieved in a number of different ways, a few examples of which are described more in detail hereinbelow.

b) Agglomeration of the culture medium might occur. As long as the reactor is floating on the expanse of water, the culture medium will be evenly distributed inside the photobioreactor. When the reactor is lowered into the surrounding water, e.g. because the temperature of the culture medium needs to be lowered or because of strong winds, this even distribution may become distorted. This problem will generally present itself by the algae culture medium collecting at one place inside the photobioreactor, thereby forming a large agglomerate. This may distort the shape and the proper functioning of the photobioreactor. In order to retain the shape and secure proper functioning of the reactor, particularly in large scale reactors, such agglomeration should be avoided.

It has been found that the problems of agglomeration and formation of large gas bubbles may be reduced or eliminated by dividing the photobioreactor into smaller sub-compartments.

In its most general embodiment, the photobioreactor comprises one large algae compartment, generally comprising a top sheet and a bottom sheet, attached to each other along the perimeters thereof to form a closed, bag-like compartment.

Figure 5:
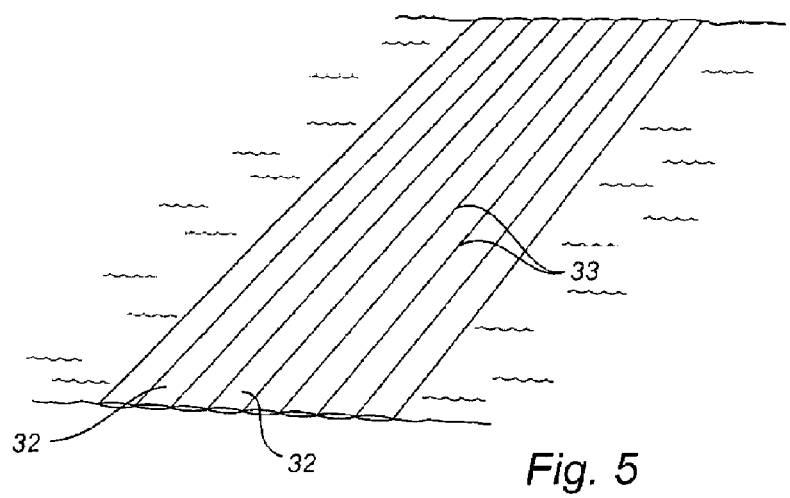
FIG. 5 shows a photobioreactor with sealed sub-compartments.

In an embodiment shown in FIG. 5, instead of the bioreactor comprising one big compartment, the algae compartment is divided into a number of different closed compartments (32) by a separator (33), which may for example be created by gluing or welding the top and bottom sheets of the photobioreactor together to form two or more smaller sub-compartments. The thus formed sub-compartments will work as an array of small photobioreactors, i.e. the culture medium with the algae can only agglomerate in one sub-compartment. As the sub-compartments have a smaller volume, large agglomerations are avoided.

The photobioreactor may also be partially divided by e.g. gluing or welding the top and bottom sheets together at specific positions. Partial divisions may restrict, but no necessarily stop entirely, the flow of culture medium and potential gas bubbles within the photobioreactor.

Figure 6A:
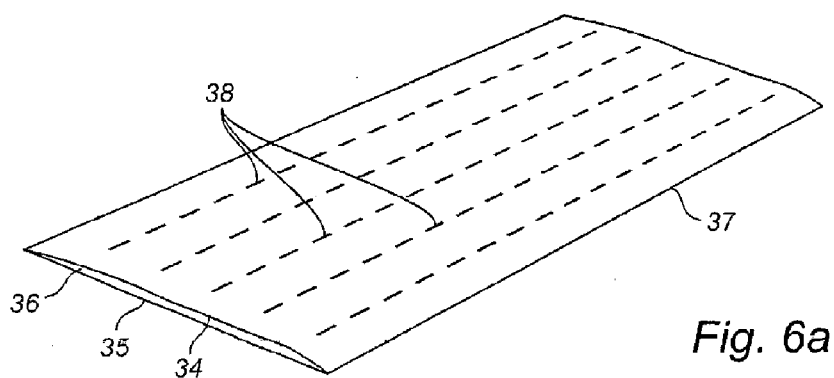
FIG. 6a is a schematic view of a photobioreactor wherein the top and bottom sheets of the reactor are connected at various points.
Figure 6B:
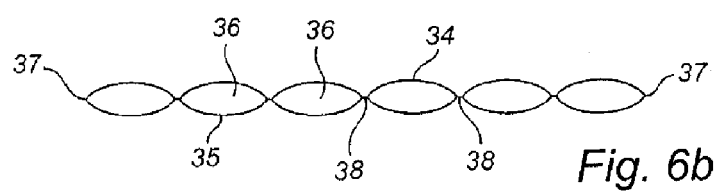
FIG. 6b is a schematic cross-sectional view of a photobioreactor wherein the top and bottom sheets of the reactor are connected at various points.
Figure 7:
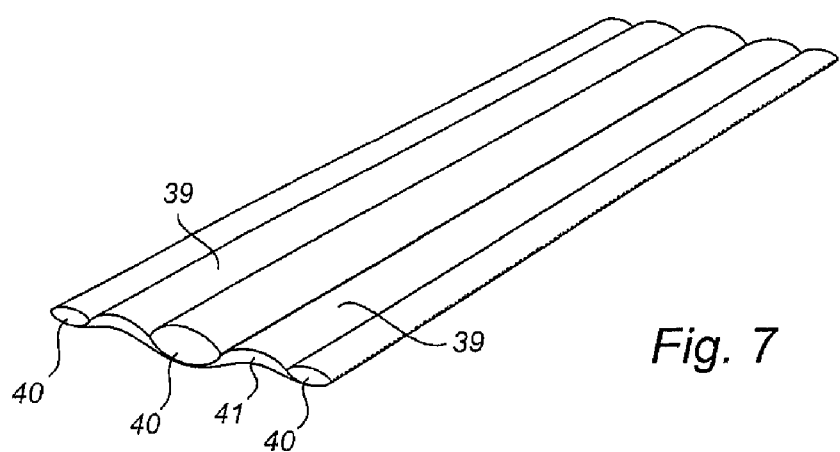
FIG. 7 is a schematic cross-sectional view of a photobioreactor with compartments on the top side of the reactor which may be filled with high density liquid to form sub-compartments inside the photobioreactor.

FIGS. 6a and 6b show embodiments of the invention wherein the photobioreactor is partially divided. The top (34) and bottom (35) sheets of the photobioreactor enclosing the algae compartment (36) are connected at the edges of the photobioreactor (37). In between, the two sheets are connected at various points (38) inside the photobioreactor, e.g. by gluing or welding. An algae compartment according to this embodiment will still have the necessary flexibility to spread out evenly when floating, but will also prevent the culture medium inside the reactor from forming large agglomerates, since the bottom and the lid layers are connected, and thereby allowing only a restricted volume of fluid in between the layers. Gluing or welding the top and bottom sheets could be performed in any number of different patterns to obtain different shapes in the formed photobioreactor sub-compartments.

Firstly, the shape of the connected areas, i.e. the gluing or welding points, may be varied. Only to provide examples without excluding other possibilities, the connection of the upper and the lower layer could be in the shape of a small circle (i.e. in the shape of a simple gluing point), e.g. with a diameter of 1 cm. The shape may also be rectangular meaning the glued or welded portion could form a complete or broken line or a portion thereof.

Secondly, the positions of the glued or welded portions inside the photobioreactor may be varied. Glued or welded points may be distributed regularly all over the reactor, or they could be concentrated at one side to ease for instance the collection of biomass or air at the other side. In the same manner, glued or welded lines could be arranged regularly so that a tube-type-pattern would be formed. Other patterns could also be constructed, e.g. such that by the provision of glued or welded lines, a flow of liquid in the photobioreactor may be predetermined. This could be compared to the structure of a Greek (English garden variety) labyrinth where there is only one potential way for the liquid to go through the reactor system. To add such a pattern could have various advantages. The definition of a certain flow direction might facilitate the harvesting of biomass or the addition of new nutrients, as this may be done at a predefined location in the reactor.

In another embodiment, the algae compartment of the photobioreactor consists of one large flexible compartment. When the photobioreactor floats on the expanse of water, this compartment reacts as one large compartment, within which liquid and gas may move freely. In order to avoid potential problems with formation of large gas bubbles or agglomeration of the culture medium when the photobioreactor is lowered into the surrounding water, the algae compartment of the photobioreactor may be temporarily partitioned into two or more different subsections before the reactor is lowered into the surrounding water. This partitioning may for example be achieved by applying force to the flexible top side of the photobioreactor such that the top sheet of the photobioreactor is pressed down towards the bottom sheet so that two or more virtual sub-compartments are formed within the algae compartment of the reactor.

The force may for example be applied by at least one elongated member, such as a rope, cable or rod arranged across the top surface of the photobioreactor and arranged to be pulled downwards. A specific embodiment is depicted in FIG. 4a. Above the photobioreactor (24) there are in regular distances ropes (25) installed, this could be done in a distance of for example every 1-2 meters. The ropes have minimum the length of the size of reactor and at both ends they are connected to vertical profiles (26). Prior to decreasing the buoyancy of the reactor, the ropes will be lowered to a position below the water surface such that the ropes will "cut" into the flexible photobioreactor such that the top sheet of the reactor is pressed down against the bottom sheet of the reactor. Virtual sub-compartments (27) are generated by the ropes, wherein the culture medium (28) tends to stay up as it still has lower density lower density than the surrounding water and does not follow the rope. When the density, and accordingly the buoyancy, of the photobioreactor is decreased and the reactor starts to sink, the virtual sub-compartments created behave as smaller separate compartments.

Various arrangements may be used in order to fix and move the ropes. In one specific embodiment, as shown in FIG. 4b, the ropes could be fixed to a T-like structure (29), which is vertically movable along a plastic or metal profile. The plastic or metal profile is vertically fixed to the ground and contains a rail where the movable structure can be moved up and down. The rope is fixed to the movable structure. To move the structure, energy and a mechanical system is required. The mechanical system could be a piston (30) at each of the profiles or one central piston could supply the mechanical force for several profiles. Each piston could be powered by pressurized gas (31). The pressurized gas may e.g. be provided by a gas tube, a compressor, or it may be pressurized $CO_2$ rich gas from an emitter, e.g. a power plant. The $CO_2$ source may preferably be the same used to for providing $CO_2$ to the culture liquid.

Another embodiment based on the general principle of temporarily partitioning the photobioreactor into two or more different subsections or compartments before the reactor is lowered into the surrounding water is shown in FIG. 8. In this embodiment the compartments (39) are not created by ropes. Instead, the compartments are created by additional compartments or tubes (40), which are located above the algae compartment (41) and which can be filled with a liquid having a higher density than the culture medium in the algae compartment of the photobioreactor. When filled with a liquid of high density, these additional compartments or tubes will sink down to press the top sheet of the photobioreactor towards the bottom sheet and create virtual sub-compartments within the algae compartment.

Itemised List of Further Embodiments

Further embodiments of the present invention are disclosed in the following numbered list of items.

1a. Photobioreactor for cultivation of phototrophic microorganisms, characterized in that
a) the photobioreactor consists of non-tubular units, represents a closed system, and is externally partially surrounded by water, so that the photobioreactor floats on a water body (e.g. an artificial pond, a river, a lake, the sea or a water filled pit), hovers in water, or is located at the ground of the water body;
b) biomass of phototropic organisms is produced, which is usable for the production of any kind of biofuels, animal feed, proteins, amino acids, of ingredients (e.g. proteins, oil) for basic human nutrition, however not for use as nutritional supplements, such as vitamins or omega-3-fatty acids.

1b. Photobioreactor for cultivation of phototrophic microorganisms for the production of fine chemicals and pharmaceuticals, characterized in that
a) the photobioreactor consists of non-tubular units, represents a closed system, and is externally partially surrounded by water, so that the photobioreactor floats on a water body (e.g. an artificial pond, a river, a lake, the sea or a water filled pit), hovers in water, or is located at the ground of the water body;
b) biomass of phototropic organisms is produced, which is used for the production of fine chemicals, nutritional supplements, vitamins, omega-3-fatty acids, antioxidants (e.g. carotenoids), pharmaceutically active substances, or dried biomass for nutritional supplementation.

2. Photobioreactor according to item 1a or 1b, characterized in that the photobioreactor consists of tubular units instead of non-tubular units.

3. Photobioreactor according to item 1a or 1b, characterized in that the photobioreactor has a flat shape (flat panel).

4. Photobioreactor according to item 1a or 1b, characterized in that the water body surrounding the photobioreactor can be used to control the temperature of the culture liquid in the photobioreactor.

5. Photobioreactor according to item 1a or 1b, characterized in that the water body surrounding the photobioreactor can be used to level out the photobioreactor so that the photobioreactor is maintained in a horizontal position.

6. Photobioreactor according to item 1a or 1b, characterized in that the water body surrounding the photobioreactor counteracts the hydrostatic inner pressure of the photobioreactor.

7. Photobioreactor according to item 1a or 1b, characterized in that the water body surrounding the photobioreactor, via the hydrostatic pressure caused by its own weight, is used to reduce the mechanical stress of the photobioreactor material.

8. Photobioreactor according to item 1a or 1b, characterized in that differences in the density (e.g. caused by salinity or temperature differences) between culture liquid in the photobioreactor and the (partially) surrounding water body are provided to control the position of the photobioreactor in the surrounding water (e.g. floating on the surface, hovering in surrounding water body, sinking in surrounding water body).

9. Photobioreactor according to item 1a or 1b, characterized in that the photobioreactor consists of a flexible material, so that the vertical thickness of culture liquid in the photobioreactor can be changed by change of the amount of culture liquid present in the photobioreactor.

10. Photobioreactor according to item 1a or 1b, characterized in that the photobioreactor can be operated on water surfaces such as lakes, rivers or seas, and therefore does not necessarily need land.

11. Photobioreactor according to item 1a or 1b, characterized in that culture medium in the photobioreactor has a horizontal velocity >0 cm/s, and is moved by an airlift, a pump or a similar device.

12. Photobioreactor according to item 1a or 1b, characterized in that the water body surrounding the photobioreactor contributes to maintenance of approximately the same vertical thickness of culture liquid in the photobioreactor over its whole horizontal dimensions.

EXAMPLE

A flexible closed flat panel photobioreactor made of a flexible polyethylene film and having the dimensions 7 meter×5 meter, was placed on the surface of a basin containing water with a salinity of 35 g/L. The algae compartment of the photobioreactor was fed with 1,800 liters of fresh water colored with methyl blue. The photobioreactor containing the colored solution (representing the culture liquid) arranged itself floating on the surface of the surrounding water, with the culture medium being homogeneously distributed over the bottom surface of the reactor.

The photobioreactor was lowered into the surrounding water by feeding water saturated with salt into an additional compartment positioned on the top side of the algae compartment. The salt water was pumped in from one side of the additional compartment only, via five liquid ports equally distributed along the longer side of the additional compartment. The reactor system started to sink at the side where the heavier salt water was pumped in. During the process as more salt water was pumped in, the additional compartment was filled completely and the other side of the algae compartment started to sink as well. When fully submerged, the photobioreactor regained its general flat panel shape.

The photobioreactor was then returned to its original position floating on the surface of the surrounding water by removing the salt water via the five liquid ports described above. To remove the salt water completely pressurized air was pushed through the additional compartment.

The invention claimed is:

1. A method for cultivating phototropic microorganisms in a photobioreactor comprising walls of a water tight, transparent, and flexible material forming a compartment, said method comprising the steps of:
providing culture liquid, gas mixture and a culture of said phototropic microorganisms in said compartment of said photobioreactor;
placing said photobioreactor on a surrounding body of water, and
exposing said photobioreactor to solar radiation to allow the phototropic microorganisms to produce biomass, wherein the internal density of the culture liquid differs from the external density of said surrounding body of water, so that the density difference causes the photobioreactor to float on top of the surrounding body of water.

2. The method according to claim 1, wherein the photobioreactor comprises two or more sub-compartments adapted to comprise the culture liquid.

3. The method according to claim 2, wherein said sub-compartments are sealed from each other.

4. The method according to claim 2, wherein said sub-compartments are connected to allow limited liquid and/or gas transport between the sub-compartments.

5. The method according to claim 2, wherein the photobioreactor is temporarily divided into two or more sub-compartments.

6. The method according to claim 1, further comprising a step of harvesting biomass.

7. The method according to claim 1, further comprising the steps of providing carbon dioxide and removing oxygen from the culture liquid.

8. The method according to claim 1, further comprising the step of providing fresh nutrients.

9. The method according to claim 1, wherein the surrounding water is an open body of water.

10. The method according to claim 1, wherein the surrounding water is a closed body of water.

11. The method according to claim 1, wherein said phototrophic microorganisms further produce fine chemicals, nutritional supplements, vitamins, omega-3-fatty acids, antioxidants, preferably carotenoids or beta-carotene, pharmeacuetically active substances, amino acids or astaxanthin.

12. The method according to claim 1, further compromising manufacturing biofuels, animal feed, proteins, amino acids, fine chemicals, nutritional supplements, vitamins, omega-3-fatty acids, antioxidants, pharmaceutically active substances or ingredients, dried biomass, or nutritional supplement from the produced biomass.

13. The method according to claim 1, wherein said internal density can be modified by changing the salinity or the temperature of the culture liquid.

14. The method according to claim 1, wherein the temperature of the culture liquid is regulated by the surrounding water.

15. The method according to claim 1, comprising a further step of dynamically adjusting the vertical position and the shape of the photobioreactor.

16. The method according to claim 15, wherein one of said one or more additional means is one or more additional compartments or tubes attached to the photobioreactor and capable of being filled with a gas or high or low density liquid.

17. The method according to claim 16, wherein submersion of the photobioreactor is accelerated by filling said one or more additional compartments or tubes with a liquid and emersion of the photobioreactor is accelerated by filling said one or more additional compartments or tubes with a gas.

18. The method according to claim 15, wherein one of said one or more additional means is mechanical means such as a net or one or more elongated members.

19. The method according to claim 1, wherein the salinity of the culture liquid and of the surronding body of water and parameters relevant for the growth of the phototrophic microorganisms can be monitored by a control unit, said control unit being operatively linked to the photobioreactor.

20. The method according to claim 1, wherein the thickness of the culture liquid in a vertical direction is between 1 and 30 cm.

* * * * *

UNITED STATES PATENT AND TRADEMARK OFFICE
CERTIFICATE OF CORRECTION

| | | |
|---|---|---|
| PATENT NO. | : 8,940,518 B2 | Page 1 of 1 |
| APPLICATION NO. | : 14/270694 | |
| DATED | : January 27, 2015 | |
| INVENTOR(S) | : Andreas Meiser et al. | |

It is certified that error appears in the above-identified patent and that said Letters Patent is hereby corrected as shown below:

In The Specification

Column 23, line 55: Replace "phototropic" with --phototrophic--;

Column 23, line 60: Replace "phototropic" with --phototrophic--; and

Column 23, line 65: Replace "phototropic" with --phototrophic--.

Signed and Sealed this
Seventh Day of July, 2015

Michelle K. Lee
*Director of the United States Patent and Trademark Office*